United States Patent
Catania et al.

(10) Patent No.: US 6,887,846 B2
(45) Date of Patent: May 3, 2005

(54) ANTIMICROBIAL AMINO ACID SEQUENCES DERIVED FROM ALPHA-MELANOCYTE-STIMULATING HORMONE

(75) Inventors: Anna Pia Catania, Milan (IT); James M. Lipton, Woodland Hills, CA (US)

(73) Assignee: Zengen, Inc., Woodland Hills, CA (US)

( * ) Notice: Subject to any disclaimer, the term of this patent is extended or adjusted under 35 U.S.C. 154(b) by 0 days.

(21) Appl. No.: 09/957,765

(22) Filed: Sep. 21, 2001

(65) Prior Publication Data

US 2002/0137685 A1 Sep. 26, 2002

Related U.S. Application Data

(63) Continuation of application No. PCT/US00/06917, filed on Mar. 7, 2000.
(60) Provisional application No. 60/126,233, filed on Mar. 24, 1999.

(51) Int. Cl.[7] .................. A01N 37/18; A61K 38/00; C07K 5/00
(52) U.S. Cl. .................. 514/2; 514/12; 530/300
(58) Field of Search .................. 514/2, 18, 12; 530/300, 350

(56) References Cited

U.S. PATENT DOCUMENTS

| | | | | |
|---|---|---|---|---|
| 5,028,592 A | * | 7/1991 | Lipton | 514/18 |
| 5,157,023 A | * | 10/1992 | Lipton | 514/18 |
| 5,739,111 A | | 4/1998 | Mahe | |
| 6,001,812 A | | 12/1999 | Mahe | |
| 2001/0018507 A1 | * | 8/2001 | Rathjen et al. | 530/387.1 |
| 2003/0109453 A1 | * | 6/2003 | Catania et al. | 514/14 |

FOREIGN PATENT DOCUMENTS

| | | |
|---|---|---|
| EP | 0972 522 A1 | 1/2000 |
| FR | 2784028 | 4/2000 |
| WO | WO/97/10838 | 3/1997 |
| WO | WO/99/58101 | 11/1999 |
| WO | PCT/US00/07846 | 3/2000 |
| WO | WO00/42856 | 7/2000 |

OTHER PUBLICATIONS

Cutuli et al., Antimicrobial effects of alpha–MSH peptides. J. Leukocyte Biol. Feb. 2000, vol. 67, No. 2, pp. 233–239.
Deeter et al. Antipyretic properties of centrally administered fragments in the rabbit. Peptides. 1989, vol. 9, pp. 1285–1288.
Hiltz et al. Alpha–MSH peptides inhibit actue inflammation and contact sensitivity. Peptdies. 1990, vol. 11, No. 5, pp. 979–982.

(Continued)

Primary Examiner—Jon Weber
Assistant Examiner—Sheridan Snedden
(74) Attorney, Agent, or Firm—Perkins Coie LLP

(57) ABSTRACT

α-MSH and other amino acid sequences derived from α-MSH were determined to have antimicrobial influences, including against two major and representative cutaneous and mucosal pathogens; *Staphylococcus aureus* and *Candida albicans*, Pharmaceutical compositions useful as antimicrobial agents, including for use in reducing the viability of microbes, reducing the germination of yeasts, killing microbes without reducing the killing of microbes by human neutrophils, for treating inflammation in which there is microbial infection without reducing microbial killing, and for increasing the accumulation of cAMP in microbes are disclosed. The antimicrobial agent is selected from the group consisting of one or more peptides including the amino acid sequence KPV, one or more peptides including the amino acid sequence MEHFRWG, or a biologically functional equivalent of any of the foregoing. The most effective of the peprides were those bearing the C-terminal amino acid sequence of α-MSH. i.e., α-MSH (1–13), (6–13), and (11–13).

31 Claims, 7 Drawing Sheets

OTHER PUBLICATIONS

Huang et al. Role of central melanocortins in endotoxin–induced anorexia. Am. J. Physio (Regulatory, Integrative & Comparative Physiology, 45) 1999 vol. 276, No. 3, pp. R864–R871.

Lipton, et al. Mechanisms of antiinflammatory action of the neuro immunomodulatory peptide alpha–MSH. Annals of the N. Y. Acad. Sci. May 1, 1998 vol. 840 pp. 373–380.

Richards et al. Effect of alpha–MSH 11–13 (Lysine–Proline–Valine) on Fever in the Rabbit. Peptides. vol. 5, pp. 815–817.

Weiss et al. Corticotropin–peptide regulation of intracellular cyclic–AMP production in cortical neurons in primary culture. J. Neurochem. 1985, vol. 45, No. 3, pp. 869–874.

Getting et al. POMC gene–derived peptides activate melanocortin type–3 receptor on murine macrophages, suppress cytokine release, and inhibit neutrophil migration in acute experimental inflammation. J. Immunol. Jun. 15, 1999. vol. 162, No. 12, pp. 7446–7453.

Harris et al. Alha–melanocyte stimulating hormone (alpha–MSH) and melanin concentrating hormone (MCH) stimulate phagocytosis by head kidney leucocytes of rainbow trout (*Oncoryhnchus mykiss*) in vitro. Fish & Shellfish Immunol. Nov. 1998, vol. 8, pp. 631–638.

U.S. Appl. No. 09/533,341, filed Mar. 23, 2000, Catania Anna P. et al.

U.S. Appl. No. 09/535,066, filed Mar. 23, 2000, Lipton.

U.S. Appl. No. 60/200,287, filed Apr. 28, 2000, Lipton.

U.S. Appl. No. 09/774,282, filed Jan. 29, 2001, Lipton.

Airaghi L., et. al., "Elevated concentrations of plasma α–MSH are associated with reduced disease progression in HIV–infected patients," J. Lab. Clin. Med. 133(3) 309–315 (1999).

Airaghi L, Lettino M, Manfredi MG, Lipton JM, Catania A. Endogenous cytokine antagonists during myocardial ischemia and thrombolytic therapy. Am. Heart J. 130: 204–211, 1995.

Airaghi L. Garofalo L. Cutuli MG. Delgado R. Carlin A. Demitri MT. Badalamenti S. Graziani G. Lipton JM. Catania A. Plasma concentrations of α–melanocyte–stimulating hormone are elevated in patients on chronic haemodialysis. Nephrology Dialysis Transplantation 15:1212–1216, 2000.

Baker, M., et. al., "The Relationship between Interleukin–6 and Herpes Simplex Virus Type–1: Implications for Behavior and Immunopathology," *Brain Behav. Immun.* 13(3):201–11 (1999).

Baker, et al., "Principles of Ambulatory Medicine" *Williams and Wilkins* (*1982*).

Barcellini, W., et al. "Inhibitory Influences of α–MSH peptides on HIV–1 expression in Monocytic cells" 12th World AIDS Conference Geneva Abstract No. 60685, Jun. 28–Jul. 3, 1998.

Barcellini W, La Maestra L, Clerici G, Garofalo L, Brini AT, Lipton JM, Catania A. α–MSH peptides inhibit HIV–1 expression in chronically infected promonocytic U1 cells and in acutely infected monocytes. Journal of Leukocyte Biology 68:693–699, 2000.

Bhattacharya A., et. al., "Effect of Cyclic AMP on RNA and Protein Synthesis in *Candida albicans,*" *Biochem, Biophysics. Res. Commun,.* 77: 1438–44 (1977).

Bickers, D., Sun–Induced Disorders, *Emergency Medicine Clinics of North America*, 3(4):659–663, 660 (1985).

Capsoni, F., et. al., "Effect of Corticosteriods on Neutrophil Function: Inhibition of Antibody–dependent Cell–Mediated Cytotoxicity (ADCC)," *J. Immunopharmacol.* 5, 217–30 (1983).

Catledge, J.D., et. al., "Clinically Significant Azole Cross–Resistance in *Candida* Isolates from HIV–Positive Patients with Oral Condidosis," *AIDS* 11:1839–44 (1997).

Catania, A., et al., "α–Melanocyte Stimulating Hormone in the Modulation of Host Reactions," *Endocr. Rev.* 14, 564–576 (1993).

Catania, A., et. al., "Melanocortin Peptides Inhibit Production of Proinflammatory Cytokines in Blood of HIV–Infected Patients," *Peptides,* 19(6): 1099–1104 (1998).

Catania, A., et. al., "The Neuropeptide α–MSH in HIV Infection and Other Conditions in Humans" *Ann. N.Y. Acad. Sci.* 840: 848–856 (1998).

Catania, A.; et al., "The Neuropeptide α–MSH has Specific Receptors on Neutrophils and Reduces Chemotaxis in Vitro," *Peptides*17, 675–679 (1996).

Catania A, Airaghi L Lipton JM. α–MSH in normal human physiology and disease states. Trends Endocrinol. Metab. 11:304–308, 2000.

Catania A, Delgado R Airaghi L, Cutuli M Garofalo L, Carlin A Demitri MT, Lipton JM. α–MSH in systemic inflammation: central and peripheral actions. Annals of the New York Academy of Sciences, 885:183–187, 1999.

Catania A, Grazia M, Manfredi MG, Airaghi L, Ceriani G, Gandino A Lipton JM. Cytokine antagonists in infectious and inflammatory disorders. Annals of the New York Academy of Sciences 741: 149–161 1994.

Catania A, Lipton JM. α–melanocyte–stimulating hormone peptides in host responses: from basic evidence to human research. Annals of the New York Academy of Sciences 680: 412–423, 1993.

Catania A, Cutli M, Garofalo L, Airaghi L, Valenza F, Lipton JM, Gattinoni L. Plasma concentrations and anti–L–cytokine effects of α–melanocyte stimulating hormone in septic patients. Crit. Care Med. 28: 1403–1407, 2000.

Catania A, Airaghi L, Motta P, Manfredi MG, Annoni G, Pettenati C, Brambilla F and Lipton JM. Cytokine antagonists in aged subjects and their relation with cellular immunity. Journal of Gerontology: Biological Sciences 52A: B93–97, 1997.

Catania A, Manfredi MG, Airaghi L, Vivirito MC, Capetti A, Milazzo F, Lipton JM and Zanussi C. Plasma concentration of cytokine antagonists in patients with HIV infection. Neuroimmunomodulation 1: 42–49, 1994.

Catania A, Airaghi L, Manfredi MG, Vivirito MC, Milazzo F, Lipton JM, Zanussi C: Proopiomelanocortin–derived peptides and cytokines: relations in patients with acquired immunodeficiency syndrome. Clinical Immunology and Immunopathology 66: 73–79, 1993.

Cavello, J. and Deleo, V., Suburn, *Dermatologic Clinics,* 4(2): 181–187, 181 (1986).

Ceriani G., et. al., "Central Neurogenic Antiinflammatory Action of α–MSH: Modulation of Peripheral Inflammation Induced by Cytokines and other Mediators of Inflammation," *Neuroendocrinology,* 59:138–143 (1994).

Ceriani G, Diaz J, Murphree S, Catania A, Lipton JM. The neuropeptide alpha–melanocyte–stimulating hormone inhibits experimental arthritis in rats. Neuroimmunomodulation 1:28–32, 1994.

Chiao H, Foster S, Thomas R, Lipton J, and Star RA. α–MSH reduces endotoxin–induced liver inflammation J. Clin. Invest. 97: 2038–2044, 1996.

Csata, M. et. al., "Enhancement of *Candida albicans* killing activity of separated human epidermal cells by alpha–melanocyte stimulating hormone," British Journal of Dermatology 121(1) 145–147 (1989).

Delgado, R., et. al., "Melanocortin peptides inhibit production of proinflammatory cytokines and nitric oxide by activated microglia," *Journal of Leukocyte Biology,* 63: 740–745 (1998).

Domk–Optiz, I., et. al., "Stimulation of Macrophages by Endotoxin Results in the Reactivation of a Persistent Herpes Simplex Virus Infection," Scand J. Immunol. 32(2):69–75 (1990).

Eberle, A. and Schwyzer R., Hormone–Receptor Interactions, *Clinical Endocrinology* 5, Suppl., 41s–48s (1976).

Eberle, A.N., The Melanotrophins, *Karger, Basel, Switzerland* (1988).

Fauci, A.S., "Host Factors in the Pathogenesis of HIV–induced Disease," Nature 384: 529 (1996).

Fitzpatrick, et al., Acute Effects of Ultraviolet Radiation on the Skin: The Sunburn Reaction, *Dermatology in General Medicine,* 4th Edition, 1651–1655, 1651 (1993).

Fitzpatrick, et al., "Color Atlas and Synopsis of Clinical Dermatology," (1983).

Foster, J. Sunburn, *eMedicine—Online Medical Reference Textbook* (last modified May 1 2000), <http://emedicine.com/emerg/topic798.htm.

Fox, J. A., et.al., "Immunoreactive α–Melanocyte Stimulating Hormone, Its Distribution in the Gastrointestinal Tract of Intact and Hypophysectomized Rats,"*Life. Sci.* 28, 2127–2132 (1981).

Galimberti D, Baron PL, Meda L, Prat E, Scarpini E, Delgado R, Catania A, Lipton JM, Scarlato G. α–MSH peptides inhibit production of nitric oxide and tumor necrosis factor–α by microglial cells activated with β–amyloid and interferon γ. Biochemical Biophysical Research Communications 263: 251–256, 1999.

Gow, N.A., "Germ Tube Growth of *Candida albicans,*" Curr. Topics Med. Myco. 8, 43–55 (1997).

Hart, D.A., et. al., "*Staphylococcus Aureus* Strains Differ in Their in Vitro Responsiveness to Human Urokinase: Evidence that Methicillin–Resistant Strains are Predominantly Nonresponsive to the Growth–Enhancing Effects of Urokinase," Can. J. Microbiol. 42: 1024–31 (1966).

"Harry's Comseticology", *Chemical Publishing, 7th ed.* (1982), pp. 59–73 & 447–469.

Hiltz, M. E., et. al., "Anti–inflammatory Acitivity of a COOH–terminal Fragment of the Neuropeptide α–MSH," *FASEB J.* 3, 2282–2284 (1989).

Hiltz, M.E., "Anti–inflammatory Activity of α–MSH (11–13) Analogs: Influences of Alterations in Stereochemistry," Peptides 12, 767–71 (1991).

Hiltz, M.E., et. al., "Alpha–MSH Peptides Inhibit Acute Inflammation and Contact Sensitivity," *Peptides,* 11:979–982 (1990).

Hiltz, M.E., et. al., "α–MSH Peptides Inhibit Acute Inflammation Induced in Mice by rIL–1β, rIL–6 rTNF–α and endogenous pyrogen but not that cause by LTB4, PAF and rIL–8," Cytokine 4(4):320–328 (1992).

Holdeman, M., et al., "Antipyretic Activity of a Potent α–MSH Analog," Peptides 6, 273–5 (1985).

Huh S–K, Lipton JM and Batjer HH. The protective effects of α–melanocyte stimulating hormone on canine brainstem ischemia. Neurosurgery 40:132–139 1997.

Ichiyama T, Sakai T, Catania A, Barsh GS, Furukawa S, Lipton JM. Systemically administered α–melanocyte–stimulating hormone peptides inhibit NF–κB activation in experimental brain inflammation. Brain Research 836: 31–37, 1999.

Ichiyama T, Zhao H, Catania A, Furukawa S, Lipton JM. α–melanocyte–stimulating hormone inhibits NF–κB activation and IαBκ degradation in human glioma cells and in experimental brain inflammation. Experimental Neurology 157:359–365, 1999.

Ichiyama T, Campbell IL, Furukawa S, Catania A, Lipton JM. Autocrine α–melanocyte–stimulating hormone inhibits NF–κB activation in human glioma cells, Journal of Neuroscience Research 58:684–689, 1999.

Ichiyama T, Okada K, Campbell IL, Furukawa S, Lipton JM. NF–κB activation is inhibited in human pulmonary epithelial cells transfected with α–melanocyte–stimulating hormone vector. Peptides 21: 1473–1477, 2000.

Ichiyama T, Sakai T, Catania A, Barsh GS, Furukawa S, Lipton JM. Inhibition of peripheral NF–κB activation by central action of α–melanocyte–stimulating hormone. Journal of Neuroimmunology 99: 211–217, 1999.

Lichtensteiger, W., and Monnet, F., "Differential Response of Dopamine Neurons to α–Melanotropin and Analogues in Relation to Their Endocrine and Behavior Potency," *Life Sci.* 25:2079–2087 (1979).

Lipton, J.M., et.al., "Anti–inflammatory Effects of the Neuropeptide α–MSH in Acute Chronic and Systemic inflammation," Ann. N.Y. Acad. Sci. 741, 137–148 (1994).

Lipton, J.M., et. al., "Anti–inflammatory Actions of the Neuroimmunomodulator α–MSH," *Immunol. Today* 18, 140–145 (1997).

Lipton, J.M., "Neuropeptide α–Melanocyte–Stimulating Hormone in Control of Fever, the Acute Phase Response, and Inflammation" *Neuroimmune Networks: Physiology and Diseases,* (Alan R. Liss, Inc. 1989) pp. 243–250.

Lipton, J.M., Modulation of Host Defense by the Neuropeptide α–MSH, *The Yale Journal of Biology and Medicine* 63: 173–182 (1990).

Lipton JM, Catania A, Ichiyama T. Marshalling the anti–inflammatory influence of the neuroimmunomodulator α–MSH. News Physiol. Sci, 15: 192–195, 2000.

Lipton JM, Catania A. The neuropeptide α–MSH: a modulator of host reactions. Seminars in Clinical Immunology 10: 25–29, 1995.

Luger, T.A., et. al., "Production of Immunosuppressing Melanotropins by Human Keratinocytes," Ann. N.Y. Acad. Sci. 680: 567–570 (1993).

Lyson, K., et. al., "Bidning of Anti–Inflammatory α–Melanocyte–Stimulating Hormone Peptides and Proinflammatory Cytokines to Receptors on Melanoma Cells," *Neuroimmunomodulation,* 1:121–126 (1994).

Macaluso, A., et. al., "Antiinflammatory Influences of α–MSH molecules: Central Neurogenic and Peripheral Actions," The Journal of Neuroscience, 14(4): 2377–2382 (1994).

Mayhall, Ten Home Remedies for Sunburn, *Seasonal Health* (Jul. 14, 2000), <http://drkoop.com/wellness/seasonal/summer/sunburn.html>.

Mugridge, K.G., et. al., "α–Melanocyte–Stimulating Hormone reduces interleukin–1 β effects on rat stomach preparations possibly through interference with type I receptor," *European Journal of Pharmacology*, 197: 151–155 (1991).

Noisakran S., e. al., "Lymphocytes Delay Kinetics of HSV–1 Reactivation from in vitro Explants of Latent Infected Trigeminal Ganglia," *J. Neuroimmunol.* 95(1–2):126–35 (1999).

Patel, A., et. al., "Herpes Simplex Type 1 Induction of Persistent NF–κB Nuclear Translocation Increases the Efficiency of Virus Replication," *Virology* 247(2):212–22 (1998).

Potts, Sunburn, Sunlight and Sunscreens, *Postgrad. med.,* 87:52–61 (1990).

Rajora, N., et.al., "α–MSH Modulates Local and Circulating tumor Necrosis Factor α in Experimental Brain Inflammation," *J. Neuroosci,* 17, 2181–2186 (1997).

Rajora, N., et. al., "α–MSH Production Receptors and Influence on Neopterin in a Human Monocyte/macrophage Cell Line," *J. Leukoc. Biol.* 59, 248–253 (1996).

Rajora N, Boccoli G, Catania A and Lipton JM. α–MSH modulates experimental inflammatory bowel disease. Peptides 18:381–385, 1997.

Remington's Pharmaceutical Sciences *Mack Publishing Co., 18$^{th}$ ed.* (1990).

Richards, D.B., et. al., "Effect of a–MSH (11–13) (lysine–proline–valine) on Fever in the Rabbit," *Peptides* 5, 815–817 (1984).

*Robbins Pathologic Basis of Disease 5$^{th}$ ed.,* Saunders Co., Philadelphia (1994) p. 335–337, 354–355, 1008, 1037–1038.

Ryan, et al., "Inflammation," *a Scope Publication, The Upjohn Company,* (1997).

Star, R.A., et. al., "Evidence of Autocrine Modulation of Macrophage Nitric Oxide Synthase by α–MSH," *Proc. Nat'l. Acad. Sci.* (*USA*) 92, 8015–8020 (1995).

Stevens, D.L., "Could Nonsteriodal Anti–inflammatory Drugs (NSAIDs) Enhance Progression of Bacterial Infections to Toxic Shock Syndrome?," *Clin. Infect. Dis.* 21, 977–80 (1997).

Szalay, K.S., et. al., "Structure–activity studies with ACTH/α–MSH fragments on corticosteroid secretion of isolated zona glomerulosa and fasciculaa cells," *Regulatory Peptides,* 11: 187–192 (1985).

Taherzadeh S, Sharma S, Chhajlani V, Gantz I, Rajora N, Demitri MT, Kelly L, Zhao H, Catania A, Lipton JM. α–MSH and its receptors in regulation of tumor necrosis factor–α production by human monocyte/macrophages. Am. J. Physiol. 276: R1289–R1294, 1999.

Thody, A.J., et.al., "MSH Peptides are Present in Mammalian Skin," *Peptides* 4, 813–815 (1983).

Uehara, Y., et. al., "Carboxyl–terminal tripeptide of α–Melanocyte–Stimulating Hormone anagonizes interluekin–1–induced anorexia" *European Journal of Pharmacology,*220: 119–122 (1992).

van Nispen, J.W. and Greven, H.M., "Structure–Activity Relationships of Peptides Derived From ACTH, β–LPH and MSH With Regard To Avoidance Behavior in Rats," *Pharmac. Ther.* 16: 67–102 (1982).

Walev, I., et. al., "Enhancement by TNF–alpha of Reactivation and Replication of Latent Herpes Simplex Virus from Trigeminal Ganglia of Mice," *Arch Virol.* 140(6):987–92 (1995).

Watanabe T, Hiltz ME, Catania A, Lipton JM. Inhibition of IL–1β–induced peripheral inflammation by peripheral and central administration of analogs of the neuropeptide α–MSH. Brain Research Bulletin 32: 311–314, 1993.

Wenzel, R.P. and Pfaller, M.A., "Candida Species: Emerging Hospital Bloodstream Pathogens," *Infect. Control. Hosp. Epidemiol.* 12: 523–4 (1991).

Wong, K.Y., et. al., "A Potential Mechanism of Local Anti–inflammatory Action of Alpha–Melanocyte–Stimulating Hormone within the Brain: Modulation of Tumor Necrosis Factor–Alpha Production by Human Astrocytic Cells," *Neuroimmunomodulation,*4:37–41 (1997).

"Vaginitis," National Institute of Child Health and Human Development—Publications On–line (last modified Jan. 12, 2000).<www.nichd.nih.gov/publications/pubs/vagtoc.html<.

"Tampons and Asbestos, Dioxins, & Toxic Shock Syndrome," FDA Center for Devices and Radiological Health (Jul. 23, 1999), <http://www.fda.gov/cdrh/ocd/tamponsabs.html>.

Khurshid, M.A., et. al., :*Staphylococcus aureus* with Reduced Susceptibility to Vancomycin—Illinois 1999, *Morbidity and Mortality Weekly Report,* 48(51): 1165–1167 (2000), <http://www.cdc.gov/epo/mmwr/preview/mmwrhthml/mm4851al.htm>.

"Women's Health, Urinary Tract Infections: A Patient's Guide to Treatment," *AMA Health Insight, On Line, Health Information for Everyone* (last updated Oct. 30, 1998) <http://www.ama–assn.org/insight/h_focus/wom_hlth/uti/uti.htm>.

* cited by examiner

FIG. 5 Influence of α-MSH peptides on *C. albicans* germination.
A) blastospores;
B) horse serum-induced germination;
C) effect of α-MSH (1-3) treatement on germination
D) effect of α-MSH (11-3) treatement on germination

US 6,887,846 B2

ANTIMICROBIAL AMINO ACID SEQUENCES DERIVED FROM ALPHA-MELANOCYTE-STIMULATING HORMONE

CROSS REFERENCE TO RELATED APPLICATION

This application is a continuation of commonly owned PCT patent application Ser. No. PCT/US00/06917 filed Mar. 17, 2000, which claims the priority of U.S. patent application Ser. No. 60/126,233 filed Mar. 24, 1999.

TECHNICAL FIELD

The present invention relates to new pharmaceutical compositions useful as antimicrobial agents, including, for example, for use in reducing the viability of microbes, reducing the germination of yeasts, killing microbes without reducing the killing of microbes by human neutrophils, for treating inflammation in which there is microbial infection without reducing microbial killing, and for increasing the accumulation of cAMP in microbes. More particularly, this invention relates to antimicrobial agents including amino acid sequences derived from alpha-melanocyte-stimulating hormone (α-MSH) and biologically functional equivalents thereof.

BACKGROUND OF THE INVENTION

Mucosal secretions, phagocytes, and other components of the nonspecific (innate) host defense system initiate the response to microbial penetration before time-consuming adaptive immunity starts. Survival of plants and invertebrates, which lack adaptive immunity, illustrates effectiveness of host defense based on such innate mechanisms.

Endogenous antimicrobial peptides are significant in epithelia, the barrier to environmental challenge that provides the first line of defense against pathogens. Production of natural antimicrobial peptides by phagocytes has been recognized for a long time. These natural antimicrobial peptides generally have a broad spectrum of activity against bacteria, fungi, and viruses. Martin, E., Ganz, T., Lehrer, R. I., *Defensins and Other Endogenous Peptide Antibiotics of Vertebrates*, J. Leukoc. Biol. 58, 128–136 (1995); Ganz, T., Weiss, J., *Antimicrobial Peptides of Phagocytes and Epithelia*, Sem. Hematol. 34, 343–354 (1997).

The search for antimicrobial peptides, however, has been painfully difficult and slow. A rare and difficult find has been bactericidal/permeability-increasing protein ("BPI"), which has been used successfully to treat children with severe meningococcal sepsis. Giroir, B. P., Quint, P. A., Barton, P., Kirsh, E. A., Kitchen, L., Goldstein, B., Nelson, B. J., Wedel, N. I., Carrol, S. F., Scannon, P. J., *Preliminary Evaluation of Recombinant Amino-terminal Fragment of Human Bactericidal/Permeability-increasing Protein in Children with Severe Meningococcal Sepsis*, Lancet 350,1439–1443 (1997).

It would be an important advance in the science to identify the most active amino acid sequences responsible for broad spectrum antimicrobial activity, which would also be useful in new prophylactic and therapeutic antimicrobial treatments.

SUMMARY OF INVENTION

According to the approach of the invention, the existence of homologs of vertebrate antimicrobial peptides in invertebrates suggests that such peptides are ancestral components of the host defense system. Some of these peptides, or their synthetic homologs, might be suggested for use as therapeutic agents for controlling microbes.

Alpha-melanocyte-stimulating hormone ("α-MSH") is an ancient 13 amino acid peptide produced by post-translational processing of the larger precursor molecule proopiomelanocortin and shares the 1–13 amino acid sequence with adrenocorticotropic hormone ("ACTH"). Eberle, A. N., *The Melanotropins*, Karger, Basel, Switzerland (1988). α-MSH is known to be secreted by many cell types including pituitary cells, monocytes, melanocytes, and keratinocytes. Lipton, J. M., Catania, A., *Anti-inflammatory Influence of the Neuroimmunomodulator α-MSH*, Immunol. Today 18, 140–145 (1997). α-MSH occurs in the skin of rats and in the human epidermis. Thody, A. J., Ridley, K., Penny, R. J., Chalmers, R., Fisher, C., Shuster, S., *MSH Peptides Are Present in Mammalian Skin*, Peptides 4, 813–816 (1983). α-MSH is also found in the mucosal barrier of the gastrointestinal tract in intact and hypophysectomized rats. Fox, J. A. E. T., Kraicer, J., *Immunoreactive α-Melanocyte Stimulating Hormone, its Distribution in the Gastrointestinal Tract of Intact and Hypophysectomized Rats*, Life. Sci. 28, 2127–2132 (1981). We recently found that human duodenal cells produce α-MSH in culture. Catania et al., unpublished. The presence in barrier organs of this ancient peptide, relatively invariant in amino acid sequence over approximately 300 million years, suggests that it may have a role in the nonspecific (innate) host defense system.

Alpha-melanocyte-stimulating hormone is known to have potent antipyretic and anti-inflammatory properties. Lipton, J. M., Antipyretic and Anti-inflammatory Lys Pro Val Compositions and Method of Use, U.S. Pat. No. 5,028,592, issued Jul. 2, 1991, which is incorporated herein by reference in its entirety; Lipton, J. M., Antipyretic and Anti-inflammatory Lys Pro Val Comoositions and Method of Use, U.S. Pat. No. 5,157,023, Oct. 20, 1992, which is incorporated herein by reference in its entirety; Catania, A., Lipton, J. M., *α-Melanocyte Stimulating Hormone in the Modulation of Host Reactions*, Endocr. Rev. 14, 564–576 (1993); Lipton, J. M., Catania, A., *Anti-inflammatory Influence of the Neuroimmunomodulator α-MSH*, Immunol. Today 18, 140–145 (1997), α-MSH reduces production of proinflammatory mediators by host cells in vitro, Rajora, N., Ceriani, G., Catania, A., Star, R. A., Murphy, M. T., Lipton, J. M. *α-MSH Production, Receptors, and Influence on Neopterin, in a Human Monocyte/macrophape Cell Line*, J. Leukoc. Biol. 59, 248–253 (1996); Star, R. A, Rajora, N., Huang, J., Stock, R. C., Catania, A., Lipton, J. M., *Evidence of Autocrine Modulation of Macrophape Nitric Oxide Svnthase by α-MSH*, Proc. Nat 7Acad. Sci. (USA) 92, 8016–8020 (1995). α-MSH also reduces production of local and systemic reactions in animal models of inflammation. Lipton, J. M., Ceriani, G., Macaluso, A., McCoy, D., Carries, K., Blltz, J., Catania, A., *Anti-inflammatory Effects of the Neuropeptide α-MSH in Acute, Chronic, and Systemic Inflammation*, Ann. N. Y. Acaci. Sci. 741, 137–148 (1994); Rajora, N., Boccoli, G., Burns, D., Sharma, S., Catania, A., Lipton, J. M., *α-MSH Modulates Local and Circulating Tumor Necrosis Factor A in Experimental Brain Inflammation*, J. Neurosci. 17, 2181–2186 (1997). The "core" α-MSH sequence (4–10) has learning and memory behavioral effects but little antipyretic and anti-inflammatory activity. Lipton, J. M., Catania, A., *Anti-inflammatory Influence of the Neuroimmunomodulator α-MSH*, Immunol. Today 18, 140–145 (1997). The active message sequence for these antipyretic and anti-inflammatory activities resides in the C-terminal amino acid sequence of α-MSH, that is, lysine-proline-valine ("Lys- Pro-Val" or "KPV" (SEQ ID NO: 1)), which has activities in vitro and in viva that parallel those of the parent molecule. Richards, D. B., Lipton, J. M., *Effect of α-MSH (11–13) (lysine-proline-valine) on Fever in the Rabbit, Peptides* 5, 815–817 (1984); Hiltz, M. E., Lipton, J. M., *Anti-inflammatory Activity of a COOH-terminal Fraament of the Neurooeptide α-MSH,* FASEB J. 3, 2282–2284 (1989). These peptides are known to have extremely low toxicity. Lipton, J. M., Catania, A., *Anti-inflammatory Influence of the Neuroimmunomodulator α-MSH, Immunol. Today,* 18, 140–145 (1997).

Melanocortin peptides, including α-MSH, ACTH, and other amino acid sequences derived from α-MSH or ACTH, have heretofore not been studied for potential antimicrobial activity, and there has been no suggestion that melanocortin peptides would have such activity.

According to the invention, it has been determined that α-MSH and certain other amino acid sequences derived from α-MSH have significant antimicrobial uses, including for example, for use in reducing the viability of microbes, reducing the germination of yeasts, killing microbes without reducing the killing of microbes by human neutrophils, for treating inflammation in which there is microbial infection without reducing microbial killing, and increasing the accumulation of cAMP in microbes.

According to a broad aspect of the invention, the antimicrobial agent is selected from the group consisting of one or more peptides including the C-terminal amino acid sequence of α-MSH that is, KPV (SEQ ID NO: 1), one or more peptides including the amino acid sequence MEHFRWG (SEQ ID NO: 2), or a biologically functional equivalent of any of the foregoing.

According to one aspect of the invention, the antimicrobial agent is selected from the group consisting of one or more peptides including the C-terminal amino acid sequence of α-MSH, that is, KPV (SEQ ID NO: 1), or a biologically functional equivalent of any of the foregoing. The KPV sequence (SEQ ID NO: 1) is the amino acid sequence α-MSH (11–13). This type of antimicrobial agent includes a dimer of the amino acid sequence KPV (SEQ ID NO: 1), such as VPKCCKPV (SEQ ID NO: 5).

According to a further aspect of the invention, the anti-microbial agent is selected from the group consisting of one or more peptides including the amino acid sequence HFRWGKPV (SEQ ID NO: 3) or a biologically functional equivalent of any of the foregoing. The HFRWGKPV (SEQ ID NO: 3) sequence is the amino acid sequence α-MSH (6–13).

According to a still further aspect of the invention, the antimicrobial agent is selected from the group consisting of one or more peptides including the amino acid sequence SYSMEHFRWGKPV (SEQ ID NO: 4) or a biologically functional equivalent of any of the foregoing. The SYSMEHFRWGKPV (SEQ ID NO: 4) sequence is the entire amino acid sequence of α-MSH (1–13).

According to yet another aspect of the invention, the antimicrobial agent is selected from the group consisting of one or more peptides including the amino acid sequence MEHFRWG (SEQ ID NO: 2) or a biologically functional equivalent of any of the foregoing. The MEHFRWG (SEQ ID NO: 2) sequence is sometimes referred to as the "core" amino acid sequence of α-MSH, that is, α-MSH (4–10).

With these aspects of the invention, it is believed that the shorter amino acid sequences tend to be more effective. Preferably, the antimicrobial agent is further selected from the group consisting of one or more peptides having an amino acid chain length of up to thirteen. Still more preferably, the antimicrobial agent is further selected from the group consisting of one or more peptides having an amino acid chain length of up to eight. Based on the experimental results obtained thus far, the tripeptide KPV (SEQ ID NO: 1) is the most effective.

According to the invention, an effective concentration of the antimicrobial agent is at least $10^{-12}$ molar, and more preferably the concentration of the antimicrobial agent is at least $10^{-6}$ molar.

It is fully expected that these peptides, which have extremely low toxicity, will be effective in animal and human subjects without adverse effect.

These and other aspects of the invention will be apparent to those persons skilled in the art upon reading the following description of the experimental evidences and discussion.

BRIEF DESCRIPTION OF THE DRAWING

The accompanying figures of the drawing are incorporated into and form a part of the specification to provide illustrative examples of the present invention and to explain the principles of the invention. The figures of the drawing are only for purposes of illustrating preferred and alternate embodiments of how the invention can be made and used. It is to be understood, of course, that the drawing is intended to represent and illustrate the concepts of the invention. The figures of the drawing are not to be construed as limiting the invention to only the illustrated and described examples. Various advantages and features of the present invention will be apparent from a consideration of the written specification and the accompanying figures of the drawing wherein.

DETAILED DESCRIPTION OF THE INVENTION

I. Materials and Methods

Peptides

Figure 1:
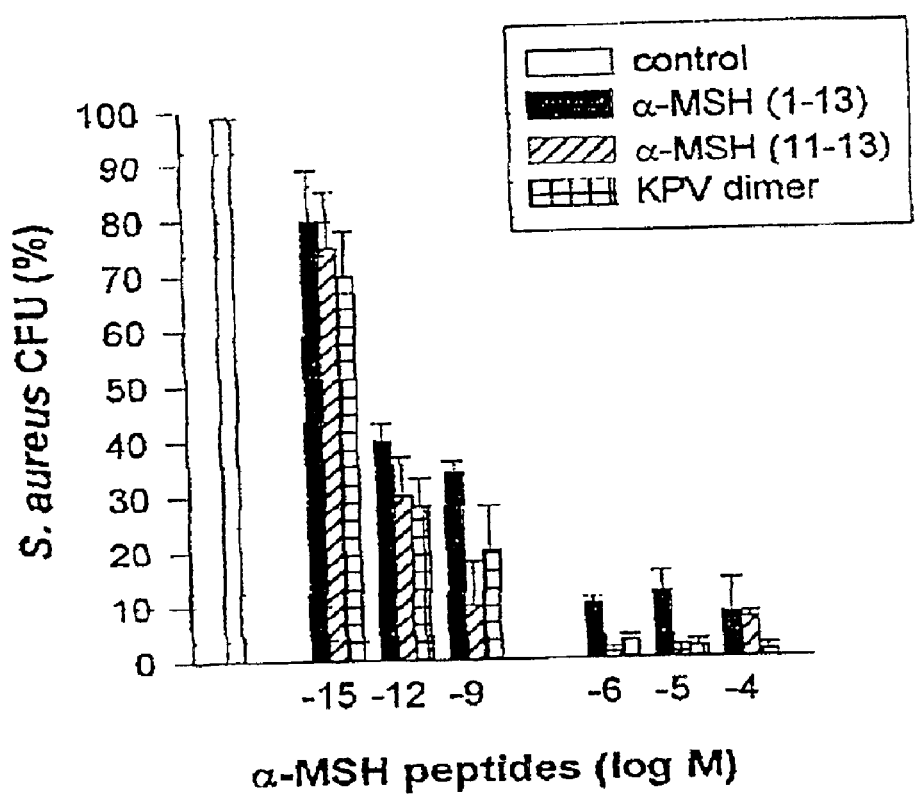
FIG. 1 shows the effect of α-MSH (1–13), α-MSH (11–13), and the "KPV dimer" on *S. aureus* colony forming units ("CFU") compared to controls. All three molecules significantly decreased *S. aureus* colony forming units over a broad range of peptide concentrations.

The peptides used in this research included: α-MSH (1–13),(4–10),(6–13), and (1113), all of which were N-acetylated and C-amidated, and ACTH (1–39) and (18–39) (CLIP). Another peptide used in this research included a dimer of the amino acid sequence KPV (SEQ ID NO: 1), specifically VPKCCKPV (SEQ ID NO: 5), which also was N-acetylated and C-amidated (the "KPV dimer"). The KPV dimer can be chemically represented as $NH_2$-Lys-Pro-Val-AcCys-CysAc-Val-Pro-Lys-$NH_2$. The peptides were prepared by solid-phase peptide synthesis and purified by reversed-phase high performance liquid chromatography, as kindly provided by Dr. Renato Longhi, CNR, Milano.

Organism and Culture Conditions

*S. aureus* (ATCC 29213) and *C. albicans* (clinical isolate) were obtained from the collection of the Department of Microbiology, Ospedale Maggiore di Milano. *C. albicans* were maintained on Sabouraud's agar slants and periodically transferred to Sabouraud's agar plates and incubated for 48 hours at 28° C. To prepare stationary growth phase yeast, a colony was taken from the agar plate and transferred into 30 ml Sabouraud-dextrose broth and incubated for 72 hours at 32° C. Cells were centrifuged at 1000×g for 10 minutes and the pellet was washed twice with distilled water. Cells were counted and suspended in Hank's balanced salt solution ("HBSS") to the desired concentration. Viability, determined by the exclusion of 0.01% methylene blue, remained >98%.

Trial of Melanocortin Peptides on *S. aureus* Viability

*S. aureus* ($1\times10^6$/ml in HBSS) was incubated in the presence or absence of α-MSH (1–13), α-MSH (11–13), or the "KPV dimer" at concentrations in the range of $10^{-15}$ to $10^{-4}$M for 2 hours at 37° C. Cells were then washed in cold distilled water and diluted with HBSS to a concentration of 100 organisms/ml. One ml aliquots were dispensed on blood agar plates and incubated for 24 hours at 37° C. Organism viability was estimated from the number of colonies formed.

In experiments on *S. aureus* we determined the influence of α-MSH on urokinase-induced growth-enhancement. Hart, D. A., Loule, T., Krulikl, W., Reno, C., *Staphylococcus Aureus Strains Differ in Their in Vitro Responsiveness to Human Urokinase: Evidence That Methicillin-resistant Strains Are Predominantly Nonresponsive to the Growth-enhancing Effects of Urokinase, Can. J. Microbiol.* 42, 1024–31 (1966). *S. aureus* ($10^6$/100 ml) were incubated for 4 hours at 37° C. with recombinant human urokinase 500 U (Lepetit, Milan, Italy) in a shaking water bath, in the presence or absence of α-MSH (1–13) or (11–13) $10^{-6}$M. Appropriate dilutions of *S. aureus* were dispensed on agar plates and colonies counted after 24 hours incubation at 37° C.

Trial of Melanocortin Peptides on *C. albicans* Viability

*C. albicans* ($1\times10^6$/ml in HBSS) was incubated in the presence or absence of α-MSH (1–13), α-MSH (11–13), or the "KPV dimer" at concentrations in the range of $10^{-15}$ to $10^{-4}$M for 2 hours at 37° C. Cells were then washed in cold distilled water and diluted with HBSS to a concentration of 100 organisms/ml. One ml aliquots were dispensed on blood agar plates and incubated for 48 hours at 37° C. Organism viability was estimated from the number of colonies formed.

In subsequent experiments using similar procedures we compared activity of α-MSH (4–10), (6–13), (11–13), ACTH (1–39), (18–39), and fluconazole, the latter being a known antifungal agent. Melanocortin peptides and fluconazole were tested in concentrations of $10^{-6}$ to $10^{-4}$M. There were at least six replicates for each concentration of peptide.

Trial of α-MSH Peptides on *C. albicans* Germination

*C. albicans* from stationary phase cultures were washed twice with distilled water and suspended in HBSS to a final concentration of $2\times10^6$/ml. Hyphal growth was induced by addition of 10% inactivated horse serum (GIBCO/BRL, Paisley, Great Britain) to yeast incubated for 45 minutes at 37° C. with continuous shaking. Horse serum was removed by washing cells twice with HBSS and incubation was continued for 60 minutes at 37° C. in the presence of α-MSH (1–13), (6–13), or (11–13) at a concentration of $10^{-6}$M with continuous shaking. The percentage of filamentous cells was evaluated under a light microscope with the aid of a hemocytometer. Experiments were run in triplicate and at least 200 cells were scored. Photomicrographs were taken with a MC100 camera attached to an Axioskop Zeiss microscope.

Trial of α-MSH Peptides on *C. albicans* Killing by Human Neutrophils

Venous blood (20 ml) from healthy volunteers was anticoagulated with heparin. Neutrophils were isolated using dextran sedimentation and Ficoll-Hypaque (Sigma Chemical Co., St. Louis, Mo., USA) centrifugation. Erythrocytes were lysed via hypotonic shock. Neutrophils represented at least 97% of the cell suspension. Cell viability, estimated by trypan blue exclusion, was >98%. Neutrophils were suspended to final concentration in HBSS.

*C. albicans* ($1\times10^6$) were opsonized with human AB serum in a shaking water bath for 30 minutes at 37° C. Organisms were then incubated with neutrophils in presence of medium alone or medium with α-MSH (1–13) or α-MSH (11–13) in concentrations of $10^{-15}$ to $10^{-4}$M in a shaking water bath for 2 hours at 37° C. After incubation, the culture tubes were placed on ice to stop growth and extracellular organisms were washed twice with centrifugation at 1000×g at 4° C. A 2.5% sodium desoxycholate solution was added to the suspension and the tubes were shaken for 5 min. Cold distilled water was added to obtain a suspension of $10^6$ cells/ml. Two 1/100 serial dilution in HBSS were made to obtain a final suspension of 100 cells/ml. Aliquots of 1 ml were dispensed on blood agar plates and incubated for 48 hours at 37° C. Colony forming units ("CFU") were counted at the end of the incubation period. Experiments were run in triplicate and repeated using blood from 5 different donors.

Trial of α-MSH Peptides on cAMP Accumulation

*C. albicans* ($10^6$/ml), permeabilized with toluene/ethanol, were incubated at 37° C. with continuous shaking in the presence of $10^{-6}$M α-MSH (1–13), (11–13), forskolin, an agent known to increase intracellular cAMP, or in medium alone. The reaction was stopped after 3 minutes by the addition of ice cold ethanol. cAMP was measured in duplicate using a commercial enzyme immunoassay (EIA) kit (Amersham, United Kingdom) after extraction via the liquid-phase method according to manufacturer's instructions. The effect of forskolin ($10^{-6}$M) on *C. albicans* colony formation was determined using the same procedures as for α-MSH peptides.

Statistical Analysis

One-way analysis of variance and Student's t test were used to analyze the data. Probability values <0.05 were considered significant.

II. Results

α-MSH Peptides Inhibited *S. aureus* Colony Formation

α-MSH peptides (1–13) and (11–13) inhibited *S. aureus* colony formation (FIG. 1). A dimer of the amino acid sequence KPV (SEQ ID NO: 1), specifically, $NH_2$-Lys-Pro-Val-AcCys-CysAc-Val-Pro-Lys-$NH_2$, (the "KPV dimer") also inhibited *S. aureus* colony formation (FIG. 1). The inhibitory effect occurred over a wide range of concentrations and was significant (p<0.01) with peptide concentrations of $10^{-2}$ to $10^{-4}$M.

Figure 2:
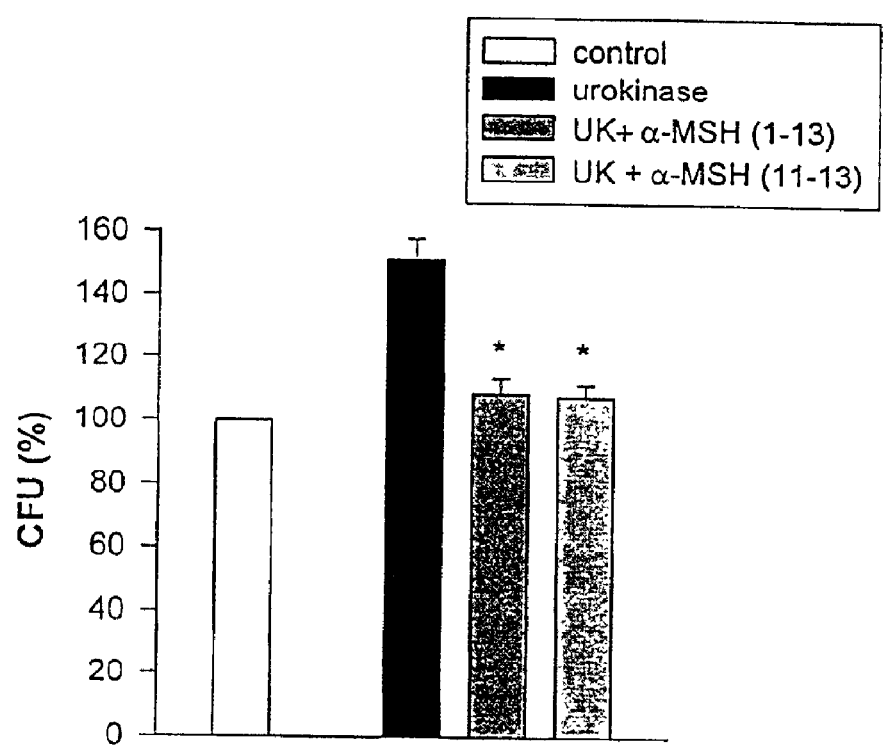
FIG. 2 shows that treatment with urokinase increases *S. aureus* colony formation, but that the addition of α-MSH (1–13) or (11–13) significantly inhibited this urokinase-enhancing effect. *$p<0.001$ vs urokinase alone.

Treatment with urokinase increased *S. aureus* colony formation and addition of α-MSH (1–13) or (11–13) at concentrations of $10^{-6}$M significantly inhibited the enhancing effect of urokinase (FIG. 2).

α-MSH Peptides Inhibited *C. albicans* Colony Formation

Figure 3:
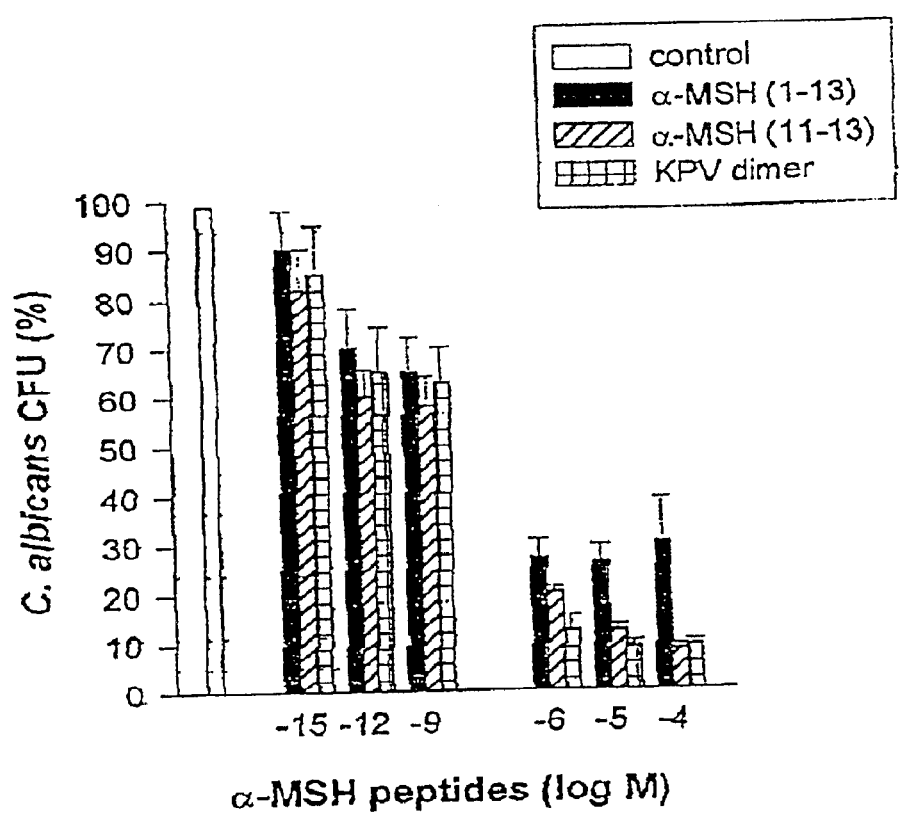
FIG. 3 shows the effect of α-MSH (1–13), α-MSH (11–13), and the "KPV dimer" on *C. albicans* colony forming units ("CFU") compared to controls. All three molecules significantly decreased *C. albicans* colony forming units over a broad range of peptide concentrations.

*C. albicans* colony forming units ("CFU") were greatly reduced by α-MSH (1–13) and (11–13) (FIG. 3). A dimer of the amino acid sequence KPV, specifically, KPVCCVPK (the "KPV dimer") also inhibited *C. albicans* colony formation (FIG. 3). Concentrations of all three peptides from $10^{-12}$ to $10^{-4}$M had significant inhibitory influences on CFU (p<0.01 vs control).

Figure 4:
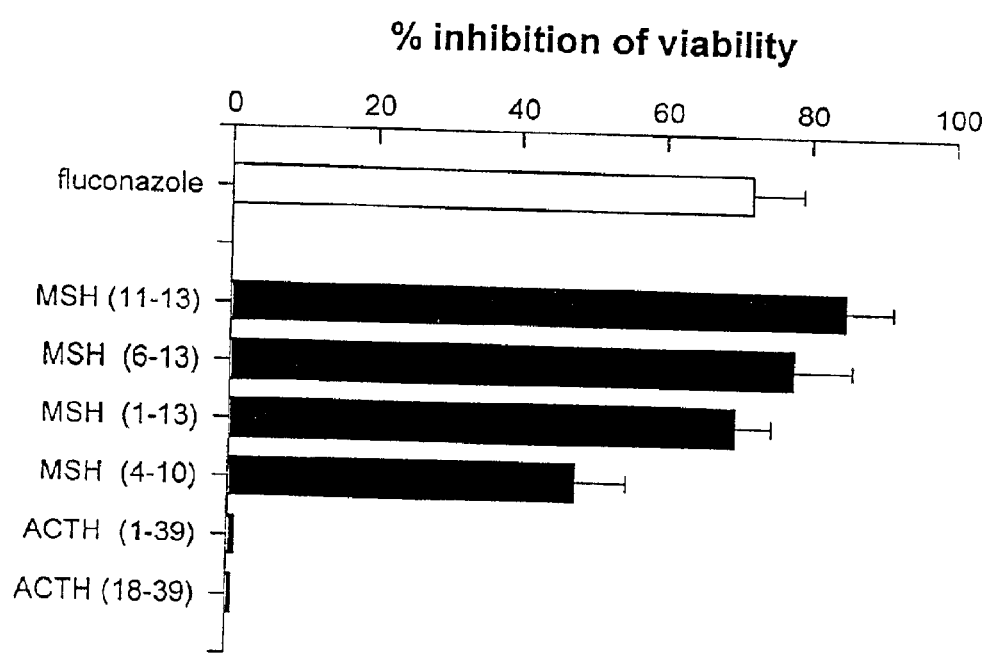
FIG. 4 shows a comparison of candidacidal activity of certain melanocortin peptides and fluconazole (all $10^{-6}$M). The most effective of the melanocortin peptides were those including the C-terminal amino acid sequence of α-MSH, for example, α-MSH (1–13), α-MSH (6–13), and α-MSH (11–13).
Figure 5:
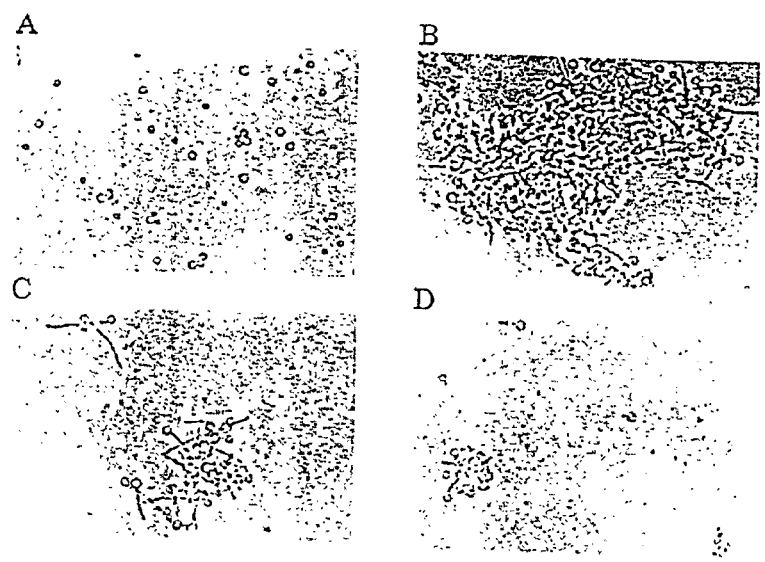
FIG. 5A shows untreated germination of *C. albicans*, i.e, blastospores.
FIG. 5B shows horse serum-induced germination of *C. albicans*.
FIG. 5C shows the effect of α-MSH (1–13) treatment on germination of *C. albicans*.
FIG. 5D shows the effect of α-MSH (11–13) treatment on germination of *C. albicans*.

In experiments comparing the relative potency of $10^{-6}$M melanocortin peptides in reducing *C. albicans* viability, α-MSH (11–13), (6–13), and (1–13) were the most effective (FIG.4). Their inhibitory activity was similar to that of equimolar fluconazole. The "core" α-MSH sequence (4–10), which has behavioral effects but little anti-inflammatory activity, caused approximately 50% inhibition of CFU. Although this inhibitory effect was substantial (p<0.01 vs control), it was significantly less than that caused by α-MSH fragments bearing the KPV signal sequence, i.e., α-MSH (6–13) and (11–13)(p<0.01), or the parent molecule α-MSH (1–13)(p<0.05). ACTH (1–39) and the ACTH fragment (18–39) did not reduce *C. albicans* viability (FIG. 4). Even higher concentrations of these ACTH peptides (up to 10–4M) were likewise ineffective in reducing *C. albicans* CFU (results not shown in the figures).

α-MSH Peptides Reduced *C. albicans* Germination

Figure 6:
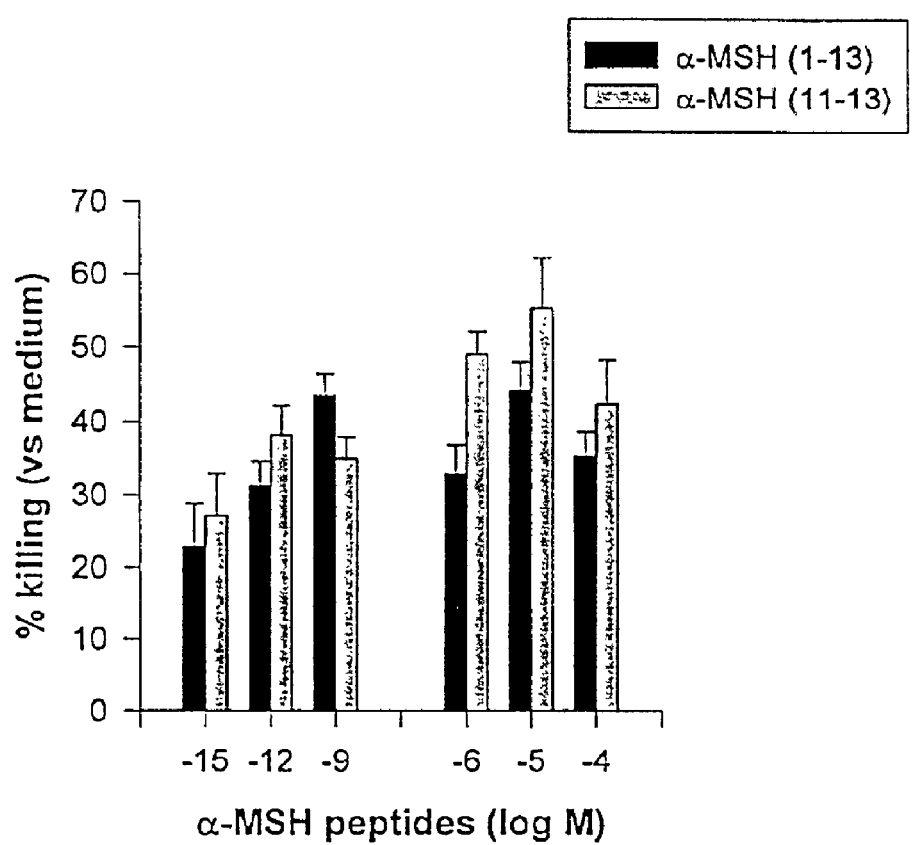
FIG. 6 shows the effect of α-MSH (1–13) and α-MSH (11–13) on *C. albicans* killing by human neutrophils. Values are expressed as percent increase in killing vs medium alone. Scores are means±SEM.

Coincubation of *C. albicans* with α-MSH (1–13) or (11–13) inhibited germ tube formation induced by horse serum (FIGS. 5A–D). α-MSH (1–13) caused 28–32% reduction in the number of filamentous cells; the tripeptide inhibited germination by 54–58%. The octapeptide α-MSH (6–13) had similar activity (approximately 50% inhibition) (not shown).

α-MSH Peptides Enhanced *C. albicans* Killing by Human Neutrophils

α-MSH (1–13) and (11–13) enhanced killing of *C. albicans* by human neutrophils when administered in concentrations of $10^{-12}$ to $10^{-4}$(p<0.01) (FIG. 6). Therefore, enhanced killing occurred over a very broad range of concentrations including picomolar concentrations, i.e., the quantity of α-MSH found in human plasma. Catania, A., Airaghi, L., Garofalo, L., Cutuli, M., Lipton, J. M., *The Neuropeptide α-MSH in AIDS and Other Conditions in Humans*, Ann. N. Y. Acad. Sci. 840, 848–856 (1998).

α-MSH Peptides Increased cAMP Accumulation

Figures 7, 8:
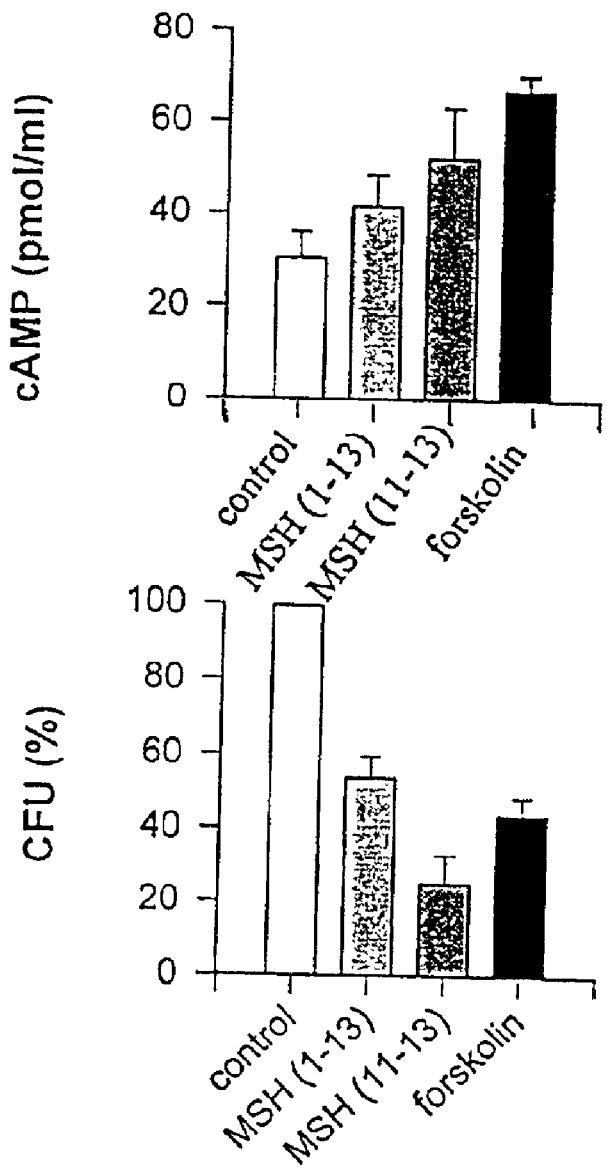
FIG. 7 shows the effect of α-MSH (1–13), α-MSH (11–13), and forskolin on cAMP content of *C. albicans*.
FIG. 8 shows the inhibitory effect of α-MSH (1–13), α-MSH (11–13), and forskolin on *C. albicans* colony forming units.

Because many of the effects of α-MSH are known to be mediated by induction of cAMP, we measured effects of α-MSH peptides on cAMP accumulation in *C. albicans*. α-MSH (1–13) and (11–13) enhanced cAMP content in the yeast (FIG. 7). The increase was of the same order of magnitude as that induced by equimolar forskolin, an adenylate cyclase activator (FIG. 7). To determine whether increases in cAMP could be responsible for reduction in CFU, we tested the effects of forskolin on *C. albicans* viability. Results showed that $10^{-6}$M forskolin markedly inhibited *C. albicans* CFU relative to control (p<0.01). The inhibitory effect was similar to that exerted by α-MSH peptides (FIG. 8).

III. Discussion

Antimicrobial Agents Against the Viability of Microbes

The results show that α-MSH (1–13), its C-terminal tripeptide sequence α-MSH (11–13), and other α-MSH fragments have significant antimicrobial effects against at least two major pathogens: *S. aureus* and *C. albicans*. The most effective of the α-MSH peptides were those including the C-terminal amino acid sequence KPV of the α-MSH sequence, i.e., α-MSH (1–13), (6–13), and (11–13). A dimer of the amino acid sequence KPV, specifically, VPKCCKPV (referred to herein as the "KPV dimer") has also been shown to be at least as effective as α-MSH (11–13) against microbes. The α-MSH "core" sequence (4–10), which is known to influence learning and memory, but has little antipyretic and anti-inflammatory influence, was effective, but less so. The ACTH peptides (1–39) and (18–39) did not have significant candidacidal effects. These observations indicate that antimicrobial activity is not common to all melanocortin peptides, but rather that it is specific to α-MSH amino acid sequences, and most particularly to the C-terminal amino-acid sequences of α-MSH.

The antimicrobial effects of these α-MSH peptides occurred over a very broad range of concentrations, including picomolar concentrations that normally occur in human plasma. Catania, A., Airaghi. L., Garofalo, L., Cutuli, M., Lipton, J. M., *The Neuropeptide α-MSH in AIDS and Other Conditions in Humans*, Ann. N. Y. Acad. Sci. 840, 848–856 (1998). This suggests that endogenous α-MSH has a physiological role in natural immunity.

Therefore, these α-MSH peptides are expected to be useful as a broad prophylactic against microbial infection and in the treatment of human and veterinary disorders resulting from microbial invasion. Further, these peptides that likewise have anti-inflammatory activity could be used to treat cases in which both inflammation and microbial invasion coexist, or where the aim is to prevent their coexistence or development.

Antimicrobial Agents Against Germination of Yeasts

Yeasts can be major pathogens. For example, *C. albicans* is the leading cause of invasive fungal disease in premature infants, diabetics, surgical patients, and patients with human immunodeficiency virus infection or other immunosuppressed conditions. Despite appropriate therapy, death resulting from systemic *C. albicans* infection in immunocompromised patients is substantial. Wenzel, R. P., Pfaller, M. A., *Candida Species: Emerging Hospital Bloodstream Pathogens*, Infect. Control Hosp. Epidemiol. 12, 523–4 (1991); Cartledge, J. D., Midgley, J., Gazzard, B. G., *Clinically Significant Azole Cross-resistance in Candida Isolates from HIV-Positive Patients with Oral Candidosis*, AIDS 11, 1839–44 (1997). The pathogenesis of *C. albicans* infection involves adhesion to host epithelial and endothelial cells and morphologic switching of yeast cells from the ellipsoid blastospore to various filamentous forms: germ tubes, pseudohyphae, and hyphae. Gow, N. A., *Germ Tube Growth of Candida Albicans*, Curr. Topics Med. Mycol. 8, 43–55 (1997). It is therefore important that α-MSH (1–13) and its C-terminal tripeptide (11–13) not only reduce the viability of yeast, but also reduce germination of yeast.

Antimicrobial and Anti-Inflammation Effects Without Reducing Killing by Human Neutrophils Reduced killing of pathogens is a dire consequence of therapy with corticosteroids and nonsteroidal anti-inflammatory drugs during infection. Stevens, D. L., *Could Nonsteroidal Anti-inflammatory Drugs (NSAIDs) Enhance Progression of Bacterial Infections to Toxic Shock Syndrome?*, Clin. Infect. Dis. 21, 977–80 (1997); Capsoni, F., Meroni, P. L., Zocchi, M. R., Plebani, A. M., Vezio, M., *Effect of Corticosteroids on Neutrophil Function: Inhibition of Antibody-dependent Cell-mediated Cytotoxicity (ADCC)*, J. Immunopharmacol. 5,217–30 (1983). This effect could be particularly dangerous in the immunocompromised host.

α-MSH has potent anti-inflammatory influences in models of acute, chronic, and systemic inflammation. Its wide spectrum of activity and low toxicity suggest that α-MSH is useful for treatment of inflammation in human and veterinary disorders. It was, therefore, important to learn the influence of α-MSH peptides on *C. albicans* killing by phagocytes. This is especially important because α-MSH is known to inhibit neutrophil chemotaxis. Catania, A., Rajora N., Capsoni, F., Minonzio, F., Star, R. A., Lipton, J. M., *The Neuropeptide α-MSH Has Specific Receptors on Neutrophils and Reduces Chemotaxis in Vitro*, Peptides 17,675–679 (1996). In the absence of trial, it could have been expected to reduce killing by human neutrophils, despite the direct antimicrobial effect. Results of the present research indicate that α-MSH peptides do not reduce killing but rather enhance it, likely as a consequence of the direct candidacidal effect. Therefore, anti-inflammatory agents such as α-MSH peptides that have antimicrobial effects are expected to be very useful in clinical practice.

Theoretical Discussion and cAMP Accumulation

An important question concerns α-MSH peptides exert their antimicrobial effects and whether they operate like other natural antimicrobial agents.

It is known that α-MSH shares a number of similarities with other natural antimicrobial peptides such as the defensins or the cathelicidins:

1) it is produced in mammals but also in primitive organisms that lack adaptive immunity. Eberle, A. N., *The Melanotropins*. Karger, Basel, Switzerland (1988).
2) like known antimicrobial peptides, its precursor molecule proopiomelanocortin (POMC) is expressed in phagocytes and epithelia and post-translational proteolytic processing is required to convert it to active α-MSH. Rajora, N., Ceriani, G., Catania, A., Star, R. A., Murphy, M. T., Lipton, J. M., *α-MSH Production, Receptors, and Influence on Neopterin, in a Human Monocyte/macrophage Cell Line*, J. Leukoc. Biol. 59, 248–253 (1996); Luger, T. A., Schauer, E., Trautinger, F., Krutmann, J., Ansel, J., Schwarz, A., Schwartz, T., *Production of Immunosuppressing Melanotropins by Human Keratinocytes*, Ann. N. Y. Acad. Sci. 680, 567–570 (1993);
3) it is a cationic peptide; and
4) it has antimicrobial influences against at least two disparate pathogens, a yeast and a bacterium. In addition, α-MSH inhibits HIV-1 replication in acutely and chronically infected monocytes. Barcellini, W., La Maestra, L., Clerici, G., Lipton, J. M., Catania, A., *Inhibitory Influences of α-MSH Peptides on Hiv-1 Expression in Monocytic Cells*, 12th World AIDS Conference, Geneva, Jun. 28–Jul. 3, 1998. These findings indicate that α-MSH has the broad spectrum of activity of other innate antimicrobial substances.

The mechanism of action of natural antimicrobial agents is only partly understood. Most of these peptides, including the defensins, alter membrane permeability and impair internal homeostasis of the organism. The first contact is made between the cationic groups of the peptide and the negatively charged head of the target membrane. Then, the tertiary structure determines the mode of insertion of the peptide into membranes where they form ion channels or pores that disrupt cell integrity. It is known that cAMP-enhancing agents inhibit mRNA and protein synthesis in *C. albicans*. Bhattacharya, A., Datta, A., *Effect of Cyclic AMP on RNA and Protein Synthesis in Candida Albicans*, Biochem. Biophys. Res. Commun. 77:1483–44 (1977).

In the present experiments it is shown that c-MSH induces cAMP accumulation in *C. albicans* and also that the cAMP-inducing agent forskolin inhibited colony formation. Without being limited by this theoretical explanation, it may be that the antimicrobial effect was caused by enhancement of this mediator.

Biologically Functional Equivalents

As used herein, a biological functional equivalent is defined as an amino acid sequence that is functionally equivalent in terms of biological activity.

Although the specific amino acid sequences described here are effective, it is clear to those familiar with the art that amino acids can be substituted in the amino acid sequence or deleted without altering the effectiveness of the peptides. Further, it is known that stabilization of the α-MSH sequence can greatly increase the activity of the peptide and that substitution of D-amino acid forms for L-forms can improve or decrease the effectiveness of peptides. For example, a stable analog of α-MSH ,[Nle$^4$,D-Phe$^7$]-α-MSH, which is known to have marked biological activity on melanocytes and melanoma cells, is approximately 10 times more potent than the parent peptide in reducing fever. Holdeman, M., and Lipton, J. M., *Antipyretic Activity of a Potent α-MSH Analog*, Peptides 6, 273–5 (1985). Further, adding amino acids to the C-terminal α-MSH (11–13) sequence can reduce or enhance antipyretic potency (Deeter, L. B., Martin, L. W., Lipton, J. M., *Antipyretic Properties of Centrally Administered α-MSH Fragments in the Rabbit*, Peptides 9, 1285–8 (1989). Addition of glycine to form the 10–13 sequence slightly decreased potency; the 9–13 sequence was almost devoid of activity, whereas the potency of the 8–13 sequence was greater than that of the 11–13 sequence. It is known that Ac-[D-K$^{11}$]-α-MSH 11–13-NH$_2$ has the same general potency as the L-form of the tripeptide α-MSH 11–13. Hiltz, M. E., Catania, A., Lipton, J. M., *Anti-inflammatory Activity of α-MSH (11–13) Analogs: Influences of Alterations in Stereochemistry*, Peptides 12, 767–71, (1991). However, substitution with D-proline in position 12 of the tripeptide rendered it inactive. Substitution with the D-form of valine in position 13 or with the D-form of lysine at position 11 plus the D-form of valine at position 13 resulted in greater anti-inflammatory activity than with the L-form tripeptide. These examples indicate that alterations in the amino acid characteristics of the peptides can influence activity of the peptides or have little effect, depending upon the nature of the manipulation.

It is also believed that biological functional equivalents may be obtained by substitution of amino acids having similar hydropathic values. Thus, for example, isoleucine and leucine, which have a hydropathic index +4.5 and +3.8, respectively, can be substituted for valine, which has a hydropathic index of +4.2, and still obtain a protein having like biological activity. Alternatively, at the other end of the scale, lysine (−3.9) can be substituted for arginine (−4.5), and so on. In general, it is believed that amino acids can be successfully substituted where such amino acid has a hydropathic score of within about +/−1 hydropathic index unit of the replaced amino acid.

Having described the invention, what is claimed is:

1. A method for reducing the viability of microbes comprising exposing the microbes to an antimicrobial agent selected from the group consisting of KPV (SEQ ID NO: 1), MEHFRWG (SEQ ID NO: 2), and HFRWGKPV (SEQ ID NO: 3) and dimers thereof.

2. A method according to claim 1, wherein the antimicrobial agent is a monomer or a dimer.

3. A method according to claim 1, wherein the antimicrobial agent is N-acetylated and C-amidated.

4. A method according to claim 1, wherein the concentration of the antimicrobial agent is at least $10^{-12}$ molar.

5. A method according to claim 4, wherein the concentration of the antimicrobial agent is at least $10^{-6}$ molar.

6. A method according to claim 1, wherein the microbes include *Staphylococcus aureus* or *Candida albicans*.

7. A method for reducing the germination of yeast comprising exposing the yeast to an antimicrobial agent selected from the group consisting of KPV (SEQ ID NO: 1) MEHFRWG (SEQ ID NO: 2) and HFRWGKPV (SEQ ID NO: 3).

8. A method according to claim 7, wherein the antimicrobial agent is N-acetylated and C-amidated.

9. A method according to claim 7, wherein the concentration of the antimicrobial agent is at least $10^{-12}$ molar.

10. A method according to claim 9, wherein the concentration of the antimicrobial agent is at least $10^{-6}$ molar.

11. A method according to claim 7, wherein the yeasts include *Candida albicans*.

12. A method for killing microbes comprising exposing the microbes to an antimicrobial agent selected from the group consisting of KPV (SEQ ID NO: 1), MEHFRWG (SEQ ID NO: 2), and HFRWGKPV (SEQ ID NO: 3) without reducing the killing of microbes by human neutrophils.

13. A method according to claim 12, wherein the antimicrobial agent is a monomer or a dimer.

14. A method according to claim 12, wherein the antimicrobial agent is N-acetylated and C-amidated.

15. A method according to claim 12, wherein the concentration of the antimicrobial agent is at least $10^{-12}$ molar.

16. A method according to claim 15, wherein the concentration of the antimicrobial agent is at least $10^{-6}$ molar.

17. A method according to claim 12, wherein the microbes include *Candida albicans* and *Staphylococcus aureus*.

18. A method for increasing the accumulation of cAMP in microbes comprising exposing the microbes to an antimicrobial agent an selected from the group consisting of KPV (SEQ ID NO: 1), MEHFRWG (SEQ ID NO: 2), HFRWGKPV (SEQ ID NO: 3), and wherein the exposure of the microbes to the antimicrobial agent increases the accumulation of cAMP.

19. A method according to claim 18, wherein the antimicrobial agent is a dimer or a monomer.

20. A method according to claim 18, wherein the antimicrobial agent excludes naturally occurring α-MSH.

21. A method according to claim 18, wherein the antimicrobial agent is further selected from the group consisting of one or more peptides having an amino acid chain length of up to thirteen.

22. A method according to claim 18, wherein the antimicrobial agent is N-acetylated and C-amidated.

23. A method according to claim 18, wherein the concentration of the antimicrobial agent is at least $10^{-12}$ molar.

24. A method according to claim 23, wherein the concentration of the antimicrobial agent is at least $10^{-6}$ molar.

25. A method according to claim 18, wherein the microbes include *Candida albicans* and *Staphylococcus aureus*.

26. A method for treating a microbial infection comprising exposing the microbes to an antimicrobial agent selected from the group consisting of KPV (SEQ ID NO: 1) MEHFRWG (SEQ ID NO: 2) and HFRWGKPV (SEQ ID NO: 3).

27. A method according to claim 26, wherein the antimicrobial agent is a monomer or a dimer.

28. A method according to claim 26, wherein the antimicrobial agent is N-acetylated and C-amidated.

29. A method according to claim 26, wherein the concentration of the antimicrobial agent is at least $10^{-12}$ molar.

30. A method according to claim 26, wherein the concentration of the antimicrobial agent is at least $10^{-6}$ molar.

31. A method according to claim 26, wherein the microbes include *Candida albicans*.

* * * * *

SEQUENCE LISTING

<160> NUMBER OF SEQ ID NOS: 5

<210> SEQ ID NO 1
<211> LENGTH: 3
<212> TYPE: PRT
<213> ORGANISM: Artificial Sequence
<220> FEATURE:
<223> OTHER INFORMATION: Designed polypeptide with anti-inflammatory,
      anti-bacterial, anti-fungal and antipyretic properties.

<400> SEQUENCE: 1

Lys Pro Val
1

<210> SEQ ID NO 2
<211> LENGTH: 7
<212> TYPE: PRT
<213> ORGANISM: Artificial Sequence
<220> FEATURE:
<223> OTHER INFORMATION: Designed polypeptide with anti-inflammatory,
      anti-bacterial, anti-fungal and antipyretic properties.

<400> SEQUENCE: 2

Met Glu His Phe Arg Trp Gly
1               5

<210> SEQ ID NO 3
<211> LENGTH: 8
<212> TYPE: PRT
<213> ORGANISM: Artificial Sequence
<220> FEATURE:
<223> OTHER INFORMATION: Designed polypeptide with anti-inflammatory,
      anti-bacterial, anti-fungal and antipyretic properties.

<400> SEQUENCE: 3

His Phe Arg Trp Gly Lys Pro Val
1               5

<210> SEQ ID NO 4
<211> LENGTH: 13
<212> TYPE: PRT
<213> ORGANISM: Artificial Sequence
<220> FEATURE:
<223> OTHER INFORMATION: Designed polypeptide with anti-inflammatory,
      anti-bacterial, anti-fungal and antipyretic properties.

<400> SEQUENCE: 4

Ser Tyr Ser Met Glu His Phe Arg Trp Gly Lys Pro Val
1               5                   10

<210> SEQ ID NO 5
<211> LENGTH: 8
<212> TYPE: PRT
<213> ORGANISM: Artificial Sequence
<220> FEATURE:
<223> OTHER INFORMATION: Designed polypeptide with anti-inflammatory,
      anti-bacterial, anti-fungal and antipyretic properties.

<400> SEQUENCE: 5

Val Pro Lys Cys Cys Lys Pro Val
1               5